(12) United States Patent
Wang et al.

(10) Patent No.: US 11,739,001 B2
(45) Date of Patent: Aug. 29, 2023

(54) MOLECULAR SIEVE COMPOSITION, PROCESS OF PREPARING SAME AND USE THEREOF

(71) Applicants: CHINA PETROLEUM & CHEMICAL CORPORATION, Beijing (CN); SHANGHAI RESEARCH INSTITUTE OF PETROCHEMICAL TECHNOLOGY SINOPEC, Shanghai (CN)

(72) Inventors: Yangdong Wang, Shanghai (CN); Haibo Zhou, Shanghai (CN); Weimin Yang, Shanghai (CN); Su Liu, Shanghai (CN); Chang Liu, Shanghai (CN); Yu Zhao, Shanghai (CN); Hongxing Liu, Shanghai (CN); Xian Lu, Shanghai (CN)

(73) Assignees: CHINA PETROLEUM & CHEMICAL CORPORATION, Beijing (CN); SHANGHAI RESEARCH INSTITUTE OF PETROCHEMICAL TECHNOLOGY SINOPEC, Shanghai (CN)

( * ) Notice: Subject to any disclaimer, the term of this patent is extended or adjusted under 35 U.S.C. 154(b) by 0 days.

(21) Appl. No.: 16/759,714

(22) PCT Filed: Oct. 23, 2018

(86) PCT No.: PCT/CN2018/111420
§ 371 (c)(1),
(2) Date: Apr. 27, 2020

(87) PCT Pub. No.: WO2019/080832
PCT Pub. Date: May 2, 2019

(65) Prior Publication Data
US 2020/0331768 A1 Oct. 22, 2020

(30) Foreign Application Priority Data
Oct. 26, 2017 (CN) .......................... 201711016754.6

(51) Int. Cl.
| | | |
|---|---|---|
| *C10G 2/00* | (2006.01) | |
| *C01B 39/54* | (2006.01) | |
| *B01J 23/06* | (2006.01) | |
| *B01J 29/83* | (2006.01) | |
| *B01J 35/00* | (2006.01) | |
| *B01J 37/08* | (2006.01) | |
| *B01J 37/03* | (2006.01) | |
| *B01J 37/10* | (2006.01) | |
| *B01J 37/06* | (2006.01) | |
| *B01J 23/26* | (2006.01) | |

(52) U.S. Cl.
CPC ............... *C01B 39/54* (2013.01); *B01J 23/06* (2013.01); *B01J 29/83* (2013.01); *B01J 35/006* (2013.01); *B01J 37/031* (2013.01); *B01J 37/06* (2013.01); *B01J 37/08* (2013.01); *B01J 37/088* (2013.01); *B01J 37/10* (2013.01); *C10G 2/332* (2013.01); *C10G 2/334* (2013.01); *B01J 23/26* (2013.01); *C01P 2002/32* (2013.01); *C01P 2002/72* (2013.01); *C10G 2300/70* (2013.01); *C10G 2400/20* (2013.01)

(58) Field of Classification Search
CPC ........ B01J 29/83; B01J 2229/42; B01J 23/06; B01J 23/26; B01J 35/006; B01J 35/002; B01J 35/023; B01J 35/0006; B01J 35/026; B01J 37/031; B01J 37/06; B01J 37/08; B01J 37/088; B01J 37/10; C01B 39/54; C01P 2002/72; C01P 2002/32; C01P 2004/52; C01P 2004/80; C01P 2004/01; Y02P 20/52; C10G 2300/70; C10G 2400/20; C10G 2/334; C10G 2/332
USPC ......... 502/214, 60, 63, 64, 67, 69, 414, 415, 502/524; 585/638
See application file for complete search history.

(56) References Cited

U.S. PATENT DOCUMENTS

| | | |
|---|---|---|
| 2007/0244000 A1 | 10/2007 | Molinier et al. |
| 2007/0297975 A1 | 12/2007 | Janssen |
| 2014/0187824 A1 | 7/2014 | Sadasivan Vijayakumari et al. |

FOREIGN PATENT DOCUMENTS

| | | |
|---|---|---|
| CN | 1083415 A | 3/1994 |
| CN | 1260823 A | 7/2000 |
| CN | 102380414 A | 3/2012 |
| CN | 102441383 A | 5/2012 |
| CN | 102698764 A | 10/2012 |

(Continued)

OTHER PUBLICATIONS

Machine translation of the claims of CN 106345514, 2017.*

(Continued)

*Primary Examiner* — Elizabeth D Wood
(74) *Attorney, Agent, or Firm* — NKL Law; Bin Lu

(57) ABSTRACT

The invention relates to a molecular sieve composition, a process of preparing same and use thereof in the production of lower olefins. The molecular sieve composition comprises an aluminophosphate molecular sieve and a CO adsorbing component, both of which are present independently of each other. When the molecular sieve composition is used as a catalyst for producing lower olefins using synthesis gas as a raw material, the molecular sieve composition has the advantages of high selectivity to lower olefins and the like.

21 Claims, 1 Drawing Sheet

(56) References Cited

FOREIGN PATENT DOCUMENTS

| CN | 106345514 A | 1/2017 |
|---|---|---|
| EP | 3632557 A1 | 4/2020 |
| WO | 2017074558 A1 | 5/2017 |

OTHER PUBLICATIONS

Machine translation of the description of CN 106345514, 2017.*
Feng Jiao et al., "Selective conversion of syngas to light olefins", Science, Mar. 2016, vol. 351, issue 6277, pp. 1065-1068.
Kirilin, Alexey V. et al.; "Conversion of Synthesis Gas to Light Olefins: Impact of Hydrogenation Activity of Methanol Synthesis Catalyst on the Hybrid Process Selectivity over Cr-Zn and Cu-Zn with SAPO-34"; Industrial & Engineering Chemistry Research; vol. 56; Sep. 21 2017; pp. 13392-13401.
Song, Huiqing et al.; "Spinel-Structured ZnCr2O4 with Excess Zn Is the Active ZnO/Cr2O3 Catalyst for High-Temperature Methanol Synthesis"; ACS Catalysis; vol. 7; Sep. 27, 2017; pp. 7610-7622.

* cited by examiner

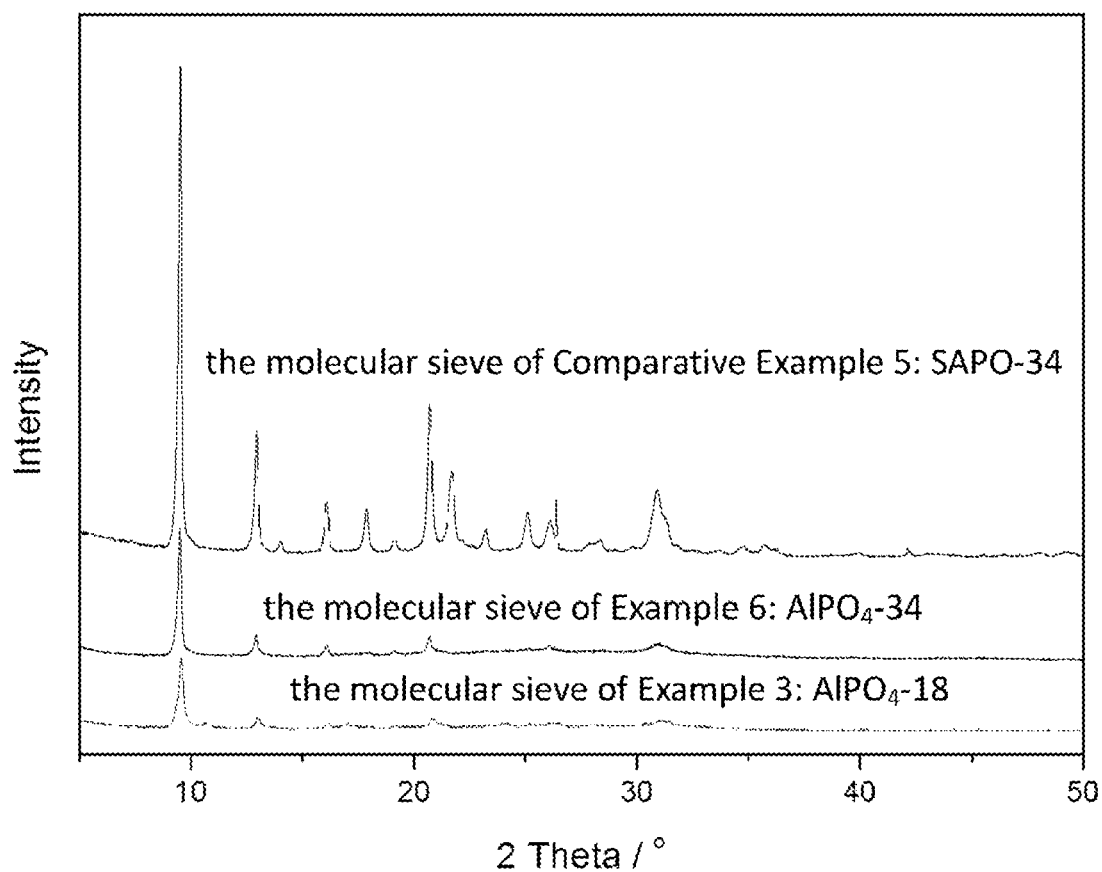

MOLECULAR SIEVE COMPOSITION, PROCESS OF PREPARING SAME AND USE THEREOF

TECHNICAL FIELD

The invention relates to a molecular sieve composition, in particular to a molecular sieve composition comprising an aluminophosphate molecular sieve and a CO adsorbing component. The invention also relates to a process of producing the molecular sieve composition and application of the molecular sieve composition in production of lower olefins.

BACKGROUND

Lower olefins, such as ethylene and propylene, are important criteria to evaluate the chemical industry level of a country. Due to the increasing scarcity of global petroleum resources, large petrochemical companies around the world are actively developing new routes to replace traditional olefin productions. Among the new routes, the process for directly preparing lower olefins from the synthesis gas has the advantages of short process flow, low energy consumption and low coal consumption, and thus is a current research hotspot and has good development prospect.

Chinese patent publication CN102698764A relates to a catalyst for preparing lower olefins from synthesis gas, a preparation process and use thereof. The catalyst comprises a main active component and an auxiliary active component, wherein the main active component comprises iron oxide and zinc oxide, and the cocatalyst component comprises potassium hydroxide or magnesium carbonate.

BAO, Xinhe et al. (Science, 2016, 351, 1065-1068) also disclose a method for the production of olefins by the hydrogenation of CO with high selectivity.

However, the technology for producing lower olefins from synthesis gas in the prior art can be further improved in view of selectivity of lower olefins.

SUMMARY OF THE INVENTION

The inventor of the invention discovers that, by using a special molecular sieve composition as a catalyst and using synthesis gas as a raw material to produce lower olefins, high selectivity of the lower olefins can be achieved with effectively reduced selectivity of by-products of lower paraffins. The present invention has been completed based on this discovery.

Specifically, the present invention relates to the following aspects.

1. A molecular sieve composition comprising an aluminophosphate molecular sieve and a CO adsorbing component, wherein the CO adsorbing component comprises at least one metal oxide selected from the group consisting of an oxide of Group IIB metal of the periodic table, an oxide of Group VIB metal of the periodic table, gallium oxide and indium oxide (preferably at least one metal oxide selected from the group consisting of zinc oxide, chromium oxide, gallium oxide and indium oxide, more preferably at least one metal oxide selected from the group consisting of zinc oxide and chromium oxide, or more preferably a composite metal oxide of zinc oxide and chromium oxide), wherein the aluminophosphate molecular sieve and the CO adsorbing component are present separately from each other, such as packed individually or mechanically mixed with each other.

2. The molecular sieve composition according to any one of the preceding or subsequent aspects, wherein the aluminophosphate molecular sieve is at least one of selected from the group consisting of $AlPO_4$-5, $AlPO_4$-11, $AlPO_4$-17, $AlPO_4$-18, $AlPO_4$-20, $AlPO_4$-31, $AlPO_4$-33, $AlPO_4$-34, $AlPO_4$-35, $AlPO_4$-44, and $AlPO_4$-56, preferably at least one selected from the group consisting of $AlPO_4$-17, $AlPO_4$-18, $AlPO_4$-31, $AlPO_4$-33, $AlPO_4$-34, $AlPO_4$-35, preferably at least one selected from $AlPO_4$-18 and $Al_4$-34, or more preferably a eutectic molecular sieve of $Al_4$-34 and $AlPO_4$-18.

3. The molecular sieve composition according to any one of the preceding or subsequent aspects, wherein the aluminophosphate molecular sieve is selected from a combination of $AlPO_4$-34 and $AlPO_4$-18, and the weight ratio of the $AlPO_4$-18 to the $AlPO_4$-34 is from 1:9 to 9:1, preferably from 1:3 to 3:1.

4. The molecular sieve composition according to any one of the preceding or subsequent aspects, wherein at least a portion (preferably 50% or more, more preferably 80% or more, or more preferably 90% or more) of the metal oxide exhibits a spinel structure according to an XRD spectrum.

5. The molecular sieve composition according to any one of the preceding or subsequent aspects, wherein the weight ratio of the aluminophosphate molecular sieve to the CO adsorbing component is from 1:5 to 5:1, preferably from 1:3 to 4:1, more preferably from 1:2 to 3:1, or more preferably from 1.5:1 to 1:1.5.

6. The molecular sieve composition according to any one of the preceding or subsequent aspects, wherein the CO adsorbing component further comprises a binder (preferably at least one selected from the group consisting of alumina, magnesia, titania and zirconia, more preferably alumina).

7. The molecular sieve composition of any preceding or subsequent aspect, wherein the weight ratio of the metal oxide to the binder is from 10:1 to 1:1, preferably from 4:1 to 1.2:1.

8. The molecular sieve composition according to any one of the preceding or subsequent aspects, being substantially free of at least one element selected from the group consisting of silicon, vanadium, and niobium.

9. The molecular sieve composition according to any one of the preceding aspects, wherein the aluminophosphate molecular sieve is present in particulate form and wherein the 90% particle diameter is from 0.3 to 9 mm (preferably from 0.4 to 5 mm, more preferably from 0.5 to 0.9 mm), and/or the CO adsorbing component is present in particulate form and wherein the 90% particle diameter is from 0.3 to 9 mm (preferably from 0.4 to 5 mm, more preferably from 0.5 to 0.9 mm).

10. A process of preparing a molecular sieve composition, comprising the step of combining an aluminophosphate molecular sieve and a CO adsorbing component (for example, packing each individually or mechanically mixing with each other, preferably mechanically mixing with each other), wherein the CO adsorbing component comprises at least one metal oxide selected from the group consisting of an oxide of Group IIB metal of the periodic table, an oxide of Group VIB metal of the periodic table, gallium oxide and indium oxide (preferably at least one metal oxide selected from the group consisting of zinc oxide, chromium oxide, gallium oxide and indium oxide, more preferably at least one metal oxide selected from the group consisting of zinc oxide and chromium oxide, or more preferably a composite metal oxide of zinc oxide and chromium oxide).

11. A process of producing lower olefins, comprising the step of contacting synthesis gas with the molecular sieve composition according to any one of the preceding aspects or the molecular sieve composition prepared by the preparation process according to any one of the preceding aspects, to produce lower olefins.

12. The process according to any one of the preceding aspects, wherein the reaction temperature is 320-480° C. (preferably 360-440° C., more preferably 370-430° C., or more preferably 380-410° C.), the reaction pressure (gauge pressure) is 0.5-8 MPa (preferably 1-6 MPa, more preferably 2-5 MPa), the gas hourly space velocity is 800-10000 (preferably 1,000-8,000 more preferably 2,000-7,000 $h^{-1}$), and the volume ratio of CO to $H_2$ in the synthesis gas is 0.3-3.5 (preferably 0.5-3, more preferably 0.7-2.5).

Technical Effect

In one embodiment, the process of producing lower olefins according to the present invention has an advantage of high selectivity to lower olefins (calculated by a ratio of lower olefins/lower paraffins).

According to the process of producing lower olefins of the present invention, in one embodiment, the ratio of lower olefins/lower paraffins is generally greater than 10, and possibly up to 26 or even higher.

DESCRIPTION OF DRAWINGS

FIG. 1 shows the XRD spectrums of the molecular sieves prepared by Example 3, Example 6 and Comparative Example 5.

EMBODIMENTS OF THE INVENTION

The embodiments of the present invention will be further illustrated in detail below, but it should be noted that the scopes of the present invention are not limited thereby, but are defined by the claims attached.

All publications, patent applications, patents, and other references mentioned in this description are herein incorporated by reference in their entirety. Unless defined otherwise, all technical and scientific terms used herein have the same meaning as commonly understood by those skilled in the art. In case of conflict, definitions provided by the present description will control.

When the description uses terms "known to those skilled in the art", "prior art", or the like, to modify materials, substances, methods, procedures, devices, or components, etc., it is intended that the subject matter modified by the terms encompasses those conventionally used in the art at the time of filing this application, but also encompasses those that are not currently in use, but would become known in the art to be suitable for similar purposes.

In the context of the present invention, the term "lower olefins" refers to a $C_2$-$C_4$ olefins and the term "lower paraffins" refers to a $C_2$-$C_4$ paraffins.

In the context of the present invention, the 90% particle diameter, measured by a manual sieving method in which the particle diameter is determined by passing the particles through sieve pores of different sizes, represents that more than 90% by weight of the particles are within a certain numerical range. The numerical range includes a lower limit and an upper limit. Specifically, for example, taking a 90% particle diameter of 0.3-9 mm as an example, it means that 90 wt % or more of the particles can pass through a sieve pore with a diameter of 9 mm but cannot pass through a sieve pore with a diameter of 0.3 mm. Other ranges of the 90% particle diameter may be similarly measured and understood.

In the context of the present description, XRD measurement is carried out using a Bruker-AXS D8 Advanced X-ray diffractometer under measurement conditions comprising: scanning with Cu KαX-ray, Ni filter, under a tube pressure of 40 kV and a tube current of 40 mA, with a scanning range of 10-60°.

Unless otherwise specifically indicated, all percentages, parts, ratios, etc. mentioned in this description are provided by weight, unless otherwise not in accordance with the conventional knowledge of those skilled in the art.

In the context of this description, any two or more aspects or embodiments of the present invention may be combined arbitrarily, and the thus resulted embodiments are parts of the original disclosure of the present description, and also fall within the protection scopes of the present invention.

According to the present invention, a molecular sieve composition is provided. The molecular sieve composition comprises an aluminophosphate molecular sieve and a CO adsorbing component.

The molecular sieve composition is particularly useful as a catalyst for producing lower olefins by using synthesis gas as a raw material.

According to an embodiment of the present invention, the aluminophosphate molecular sieve are not particularly limited, while specific examples thereof include AlPO4-5, AlPO4-11, AlPO4-17, AlPO4-18, AlPO4-20, AlPO4-31, AlPO4-33, AlPO4-34, AlPO4-35, AlPO4-44 and AlPO4-56, more specific examples thereof include AlPO4-17, AlPO4-18, AlPO4-31, AlPO4-33, AlPO4-34 and AlPO4-35, and still more specific examples thereof include AlPO4-18 and AlPO4-34. These aluminophosphate molecular sieves may be used alone or in combination of two or more in any ratio. Further, such aluminophosphate molecular sieves are commercially available as they are, or can be prepared by any method known in the art, for which the present invention does not provide any particular limitation thereto.

According to an embodiment of the present invention, in view of achieving a higher selectivity of lower olefins, a combination of AlPO4-34 and AlPO4-18, particularly a eutectic molecular sieve of AlPO4-34 and AlPO4-18, may be particularly provided as the aluminophosphate molecular sieve. The invention does not provide any particular limitation with respect to the relative ratio of AlPO4-34 to AlPO4-18 in the combination, but the weight ratio of AlPO4-18 to AlPO4-34 is generally from 1:9 to 9:1, preferably from 1:3 to 3:1. The eutectic molecular sieve may be directly commercially available or may be prepared according to any method known in the art, which is not particularly limited by the present invention.

According to an embodiment of the invention, the aluminophosphate molecular sieve is present in particulate form. In addition, in view of achieving a higher selectivity to lower olefins, the 90% particle diameter of the aluminophosphate molecular sieve is generally from 0.3 to 9 mm, preferably from 0.4 to 5 mm.

According to an embodiment of the invention, the CO adsorbing component comprises a metal oxide, or according to a particular embodiment, the CO adsorbing component is the metal oxide. Here, examples of the metal oxide include oxides of Group IIB metals of the periodic table, oxides of Group VIB metals of the periodic table, gallium oxide, and indium oxide. As the metal oxide, zinc oxide, chromium oxide, gallium oxide, and indium oxide are preferable, while zinc oxide and chromium oxide are more preferable, and a composite metal oxide of zinc oxide and chromium oxide is more preferable. These metal oxides may be used alone or in combination in any ratio. Further, such metal oxides are commercially available as they are, or can be prepared by any method known in the art, are not particularly limited by the present invention.

According to an embodiment of the present invention, in the CO adsorbing component, the metal oxide is at least partially (preferably 50% or more, more preferably 80% or more, more preferably 90% or more) present in a spinel structure. The spinel structure can be identified by an XRD method in a manner known in the art.

According to an embodiment of the present invention, the CO adsorbing component may further comprise a binder in addition to the metal oxide. As the binder, there may be mentioned, for example, any binder conventionally used in the art for preparing a metal oxide catalyst, such as refractory metal oxides, more specifically, alumina, magnesia, titania and zirconia, more particularly alumina. These binders may be used alone or in combination in any ratio. Further, the CO adsorbing component comprising the binder may be directly commercially available or may be prepared according to any method known in the art, which is not particularly limited by the present invention. In addition, although the content of the binder in the CO adsorbing component the present invention is not particularly limited, the weight ratio of the metal oxide to the binder in the CO adsorbing component is generally 10:1 to 1:1, preferably 4:1 to 1.2:1.

According to an embodiment of the invention, the CO adsorbing component is present in particulate form. In addition, in view of achieving a more desirable selectivity to lower olefins, the 90% particle diameter of the CO adsorbing component are generally 0.3 to 9 mm, preferably 0.4 to 5 mm.

According to an embodiment of the invention, the aluminophosphate molecular sieve and the CO adsorbing component are present separately from each other, that is, in an independent form from each other. The independent form may be, for example, a form in which the aluminophosphate molecular sieve and the CO adsorbing component are physically combined (in a predetermined relative ratio) after being prepared separately, and more specifically, a form in which the aluminophosphate molecular sieve and the CO adsorbing component are packed individually (in a predetermined relative ratio), or a form in which the aluminophosphate molecular sieve and the CO adsorbing component are mechanically mixed (in a predetermined relative ratios) with each other, or the like.

According to an embodiment of the present invention, the relative ratio (e.g., weight ratio) of the aluminophosphate molecular sieve to the CO adsorbing component is not particularly limited, but is generally from 1:5 to 5:1, preferably from 1:3 to 4:1, more preferably from 1:2 to 3:1, or more preferably from 1.5:1 to 1:1.5.

According to an embodiment of the present invention, in view of achieving a more desirable selectivity to lower olefins, the molecular sieve composition (including the constituent components thereof, such as the aluminophosphate molecular sieve and the CO adsorbing component) is substantially free of silicon, vanadium or niobium. By "substantially free of" it is meant that the molecular sieve composition or the constituent components thereof are not intentionally incorporated with silicon, vanadium or niobium during preparation or use, whilst very low content (e.g. less than 0.01 wt % in an oxide, relative to the total weight of the molecular sieve composition) of silicon, vanadium or niobium in a form of unavoidable impurities are not excluded.

According to an embodiment of the invention, the invention also relates to a process of preparing said molecular sieve composition. Here, the preparation process includes the step of combining the aluminophosphate molecular sieve and the CO adsorbing component. The combination may be, for example, a physical combination (in a predetermined relative ratio) of the aluminophosphate molecular sieve and the CO adsorbing component after being prepared separately, and more specifically, a combination in which the aluminophosphate molecular sieve and the CO adsorbing component (in a predetermined relative ratio) are packed individually, or a combination in which the aluminophosphate molecular sieve and the CO adsorbing component (in a predetermined relative ratio) are mechanically mixed with each other, or the like.

According to an embodiment of the invention, the invention also relates to a process of producing lower olefins, comprising the step of contacting synthesis gas with the molecular sieve composition according to any of the invention mentioned above, to produce lower olefins. The process of producing the lower olefins, except for the following exemplary ones, may be carried out in any manner known in the art and in any reaction apparatus known in the art, without any particular limitation.

According to an embodiment of the present invention, the reaction temperature for the process of producing lower olefins is not particularly limited, and may refer to the knowledge conventionally known in the art, which is however generally 320-480° C., preferably 360-440° C., more preferably 370-430° C., or more preferably 380-410° C.

According to an embodiment of the present invention, the reaction pressure (gauge pressure) of the process for producing lower olefins is not particularly limited, and may refer to the knowledge conventionally known in the art, which is however generally in the range of 0.5 to 8 MPa, preferably 1 to 6 MPa, more preferably 2 to 5 MPa.

According to an embodiment of the present invention, the gas hourly space velocity of the process for producing lower olefins is not particularly limited, and may refer to the knowledge conventionally known in the art, which is however generally 800-10000 $h^{-1}$, preferably 1,000-8,000 $h^{-1}$, more preferably 2,000-7,000 $h^{-1}$.

According to an embodiment of the present invention, the composition of the synthesis gas useful in the process for producing lower olefins is not particularly limited, and may refer to the knowledge conventionally known in the art, while the volume ratio of CO to $H_2$ in the synthesis gas is generally 0.3 to 3.5, preferably 0.5 to 3, or more preferably 0.7 to 2.5. In addition, the synthesis gas may further contain impurities, such as $CO_2$ and $N_2$, in amounts acceptable to those skilled in the art, which are not particularly limited.

EXAMPLES

The present invention will be described in further detail with reference to the Examples below, whilst the present invention is not limited to these Examples.

In the following Examples and Comparative Examples, all reagents and materials are commercially available.

In the following Examples and Comparative Examples, % is provided in weight %, space velocity indicates a gas hourly space velocity, pressure indicates a gauge pressure, and $n_{H2}:n_{CO}$ indicates molar ratio, unless otherwise specified.

In the context of the present description, including the Examples and Comparative Examples below, the CO conversion=(inlet CO content-outlet CO content)/inlet CO content*100%

In the context of the present description, including the Examples and Comparative Examples below, the olefins/paraffins ratio (indicating the lower olefins/lower paraffins ratio) is calculated according to the following equation.

Olefins/paraffins ratio=(2*moles of ethylene product+3*moles of propylene product+4*moles of butene product)/(2*moles of ethane product+3*moles of propane product+4*moles of butane product)

Example 1

$Ga_2O_3+Cr_2O_3$ catalyst was prepared by the following steps:

1 mol of gallium nitrate was weighed, dissolved with 1000 mL of distilled water. Then, 3.2 mol of NaOH was dissolved in 1000 mL of water. The two aqueous solutions were combined and co-precipitated, then aged for 3 hours at 70° C., filtered, dried overnight at 100° C., and roasted 12 hours at 400° C., to obtain the $Ga_2O_3$ catalyst.

1 mol of chromic nitrate was weighed, and dissolved with 1000 mL of distilled water. Then, 3.2 mol of NaOH was dissolved in 1000 mL of water. The two aqueous solutions were combined and co-precipitated, then aged for 3 hours at 70° C., filtered, dried overnight at 100° C., and roasted for 12 hours at 400° C., to obtain the $Cr_2O_3$ catalyst.

$AlPO_4$-5 catalyst was prepared by the following steps:

Pseudo-boehmite, phosphoric acid and tri-n-propylamine (TPA) were respectively used as an aluminum source, a phosphorus source and a template agent, with molar ratios of $Al_2O_3:P_2O_5:TPA:ethanol:H_2O=1:1.2:2.66:80:1000$, which were added into a reactor and then aged for 2 hours, and crystallized under stirring for 48 hours at 190° C. The obtained solid was washed to be neutral with deionized water, separated to obtain solid, dried, and roasted for 6 hours at 550° C. in a muffle furnace, to obtain the $AlPO_4$-5 molecular sieve.

All the formed catalysts had a 90% particle diameter of 0.5 to 0.9 mm.

0.375 g of the prepared $Ga_2O_3$ catalyst, 0.375 g of the prepared $Cr_2O_3$ catalyst and 0.75 g of the prepared $AlPO_4$-5 were mixed and put into a quartz reaction tube with an inner diameter of 6 mm. Synthesis gas ($n_{H2}:n_{CO}$=50:50) was introduced into the reaction tube to enter the catalytic bed for reaction, with a reaction temperature of 400° C., a reaction system pressure of 4 MPa, and a gas hourly space velocity of 4,000 $h^{-1}$, so as to carry out the reaction of producing lower olefins with synthesis gas. The results of the activity evaluation were shown in Table 1.

Example 2

$Cr_2O_3$ catalyst was prepared as in Example 1.

$AlPO_4$-17 catalyst was prepared by the following steps:

Pseudo-boehmite, phosphoric acid and cyclohexylamine were respectively used as an aluminum source, a phosphorus source and a template agent, with molar ratios of $Al_2O_3:P_2O_5:CHA:HF:H_2O=1:1:1:1:40$, which were added into a reactor and then aged for 2 hours, and crystallized under stirring for 72 hours at 200° C. The obtained solid was washed to be neutral with deionized water, separated to obtain solid, dried, and roasted for 6 hours at 550° C. in a muffle furnace, to obtain the $AlPO_4$-17 molecular sieve.

All the formed catalysts had a 90% particle diameter of 0.5 to 0.9 mm. 0.75 g of the prepared $Cr_2O_3$ catalyst and 0.75 g of the prepared $AlPO_4$-17 were mixed and put into a quartz reaction tube with an inner diameter of 6 mm. Synthesis gas ($n_{H2}:n_{CO}$=50:50) was introduced into the reaction tube to enter the catalytic bed for reaction, with a reaction temperature of 400° C., a reaction system pressure of 4 MPa, and a gas hourly space velocity of 4,000 so as to carry out the reaction of producing lower olefins with synthesis gas. The results of the activity evaluation were shown in Table 1.

Example 3

$ZnIn_{0.3}$ catalyst was prepared by the following steps:

1 mol of zinc nitrate and 0.3 mol of indium nitrate were weighed, and dissolved with 1000 mL of distilled water. Then, 3 mol of NaOH was dissolved in 1000 mL of water. The two aqueous solutions were combined and co-precipitated, then aged for 3 hours at 70° C., filtered, dried overnight at 100° C., and roasted for 12 hours at 400° C., to obtain the ZnIn0.3 catalyst.

$AlPO_4$-18 catalyst was prepared by the following steps:

Pseudo-boehmite, phosphoric acid and N,N-diisopropylethylamine were respectively used as an aluminum source, a phosphorus source and a template agent, with molar ratios of $Al_2O_3:P_2O_5:TPA:H_2O=1:1:1:50$, which were added into a reactor and then aged for 2 hours, and crystallized under stirring for 48 hours at 200° C. The obtained solid was washed to be neutral with deionized water, separated to obtain solid, dried, and roasted for 6 hours at 550° C. in a muffle furnace, to obtain the $AlPO_4$-18 molecular sieve.

All the formed catalysts had a 90% particle diameter of 0.5 to 0.9 mm.

0.75 g of the prepared $ZnIn_{0.3}$ catalyst and 0.75 g of the prepared $AlPO_4$-18 were mixed and put into a quartz reaction tube with an inner diameter of 6 mm. Synthesis gas ($n_{H2}:n_{CO}$=50:50) was: n introduced into the reaction tube to enter the catalytic bed for reaction, with a reaction temperature of 400° C., a reaction system pressure of 4 MPa, and a gas hourly space velocity of 4,000 so as to carry out the reaction of producing lower olefins with synthesis gas. The results of the activity evaluation were shown in Table 1.

Example 4

$Ga_2O_3$ catalyst was prepared as in Example 1.

$Zn_2Cr$ catalyst was prepared by the following steps:

2 mol of zinc nitrate and 1 mol of chromic nitrate were weighed, and dissolved with 1000 mL of distilled water. Then, 7 mol of NaOH was dissolved in 1000 mL of water. The two aqueous solutions were combined and co-precipitated, then aged for 3 hours at 70° C., filtered, dried overnight at 100° C., and roasted for 12 hours at 400° C., to obtain the $Zn_2Cr$ catalyst.

$AlPO_4$-20 catalyst was prepared by the following steps:

Pseudo-boehmite, phosphoric acid and tetramethyl ammonium hydroxide were respectively used as an aluminum source, a phosphorus source and a template agent, with molar ratios of $Al_2O_3:P_2O_5:TMAOH:H_2O=1:1:1:50$, which were added into a reactor and then aged for 2 hours, and crystallized under stirring for 48 hours at 200° C. The obtained solid was washed to be neutral with deionized water, separated to obtain solid, dried, and roasted for 6 hours at 550° C. in a muffle furnace, to obtain the $AlPO_4$-20 molecular sieve.

All the formed catalysts had a 90% particle diameter of 0.5 to 0.9 mm.

0.25 g of the prepared $Ga_2O_3$ catalyst, 0.5 g of the prepared $Zn_2Cr$ catalyst, and 0.75 g of the prepared $AlPO_4$-20 were mixed and put into a quartz reaction tube with an inner diameter of 6 mm. Synthesis gas ($n_{H2}:n_{CO}$=50:50) was introduced into the reaction tube to enter the catalytic bed for reaction, with a reaction temperature of 400° C., a reaction system pressure of 4 MPa, and a gas hourly space velocity of 4,000 $h^{-1}$, so as to carry out the reaction of producing lower olefins with synthesis gas. The results of the activity evaluation were shown in Table 1.

Example 5

$ZnCr_{0.8}In_{0.2}$ catalyst was prepared by the following steps:
1 mol of zinc nitrate, 0.8 mol of chromic nitrate and 0.2 mol of indium nitrate were weighed, and dissolved with 1000 mL of distilled water. Then, 5 mol of NaOH was dissolved in 1000 mL of water. The two aqueous solutions were combined and co-precipitated, then aged for 3 hours at 70° C., filtered, dried overnight at 100° C., and roasted for 12 hours at 400° C., to obtain the $ZnCr_{0.8}In_{0.2}$ catalyst.

$AlPO_4$-31 catalyst was prepared by the following steps:
Pseudo-boehmite, phosphoric acid and di-n-butylamine were respectively used as an aluminum source, a phosphorus source and a template agent, with molar ratios of $Al_2O_3$:$P_2O_5$:DBA:$H_2O$=1:1:1.4:40, which were added into a reactor and then aged for 2 hours, and crystallized under stirring for 2 hours at 170° C. The obtained solid was washed to be neutral with deionized water, separated to obtain solid, dried, and roasted for 6 hours at 550° C. in a muffle furnace, to obtain the $AlPO_4$-31 molecular sieve.

All the formed catalysts had a 90% particle diameter of 0.5 to 0.9 mm.

0.75 g of the prepared $ZnCr_{0.8}In_{0.2}$ catalyst and 0.75 g of the prepared $AlPO_4$-31 were mixed and put into a quartz reaction tube with an inner diameter of 6 mm. Synthesis gas ($n_{H2}:n_{CO}$=50:50) was introduced into the reaction tube to enter the catalytic bed for reaction, with a reaction temperature of 400° C., a reaction system pressure of 4 MPa, and a gas hourly space velocity of 4,000 $h^{-1}$, so as to carry out the reaction of producing lower olefins with synthesis gas. The results of the activity evaluation were shown in Table 1.

Example 6

$Zn_{0.7}Cr$ catalyst was prepared by the following steps:
0.7 mol of zinc nitrate and 1 mol of chromic nitrate were weighed, and dissolved with 1000 mL of distilled water. Then, 5 mol of NaOH was dissolved in 1000 mL of water. The two aqueous solutions were combined and co-precipitated, then aged for 3 hours at 70° C., filtered, dried overnight at 100° C., and roasted for 12 hours at 400° C., to obtain the $Zn_{0.7}Cr$ catalyst.

$AlPO_4$-34 catalyst was prepared by the following steps:
Pseudo-boehmite, phosphoric acid and morpholine were respectively used as an aluminum source, a phosphorus source and a template agent, with molar ratios of $Al_2O_3$:$P_2O_5$:Mor:HF:$H_2O$=1:1:2.0:0.5:100, which were added into a reactor and then aged for 2 hours, and crystallized under stirring for 24 hours at 180° C. The obtained solid was washed to be neutral with deionized water, separated to obtain solid, dried, and roasted for 6 hours at 550° C. in a muffle furnace, to obtain the $AlPO_4$-34 molecular sieve.

All the formed catalysts had a 90% particle diameter of 0.5 to 0.9 mm.

0.75 g of the prepared $Zn_{0.7}Cr$ catalyst and 0.75 g of the prepared $AlPO_4$-34 were mixed and put into a quartz reaction tube with an inner diameter of 6 mm. Synthesis gas ($n_{H2}:n_{CO}$=50:50) was introduced into the reaction tube to enter the catalytic bed for reaction, with a reaction temperature of 400° C., a reaction system pressure of 4 MPa, and a gas hourly space velocity of 4,000 $h^{-1}$, so as to carry out the reaction of producing lower olefins with synthesis gas. The results of the activity evaluation were shown in Table 1.

Example 7

$Zn_{0.2}/ZnCr_2$ catalyst was prepared by the following steps:
1 mol of zinc nitrate and 2 mol of chromic nitrate were weighed, and dissolved with 1000 mL of distilled water. Then, 8 mol of NaOH was dissolved in 1000 mL of water. The two aqueous solutions were combined and co-precipitated, then aged for 3 hours at 70° C., filtered, dried overnight at 100° C., and roasted for 12 hours at 400° C. After roasting, the catalyst intermediate was loaded with 0.2 mol of zinc acetate, dried at 80° C. overnight, and roasted at 400° C. for 1 h to obtain the $Zn_{0.2}/ZnCr_2$ catalyst.

$AlPO_4$-5 catalyst was prepared as in Example 1.

All the formed catalysts had a 90% particle diameter of 0.5 to 0.9 mm.

0.75 g of the prepared $Zn_{0.2}/ZnCr_2$ catalyst and 0.75 g of the prepared $AlPO_4$-5 were mixed and put into a quartz reaction tube with an inner diameter of 6 mm. Synthesis gas ($n_{H2}:n_{CO}$=50:50) was introduced into the reaction tube to enter the catalytic bed for reaction, with a reaction temperature of 400° C., a reaction system pressure of 4 MPa, and a gas hourly space velocity of 4,000 so as to carry out the reaction of producing lower olefins with synthesis gas. The results of the activity evaluation were shown in Table 1.

Example 8

$ZnCr_{0.9}Al_{0.3}$ catalyst was prepared by the following steps:
1 mol of zinc nitrate, 0.9 mol of chromic nitrate and 0.3 mol of aluminum nitrate were weighed, and dissolved with 1000 mL of distilled water. Then, 6 mol of NaOH was dissolved in 1000 mL of water. The two aqueous solutions were combined and co-precipitated, then aged for 3 hours at 70° C., filtered, dried overnight at 100° C., and roasted for 12 hours at 400° C., to obtain the $ZnCr_{0.9}Al_{0.3}$ catalyst.

$AlPO_4$-5 catalyst was prepared as in Example 1.

All the formed catalysts had a 90% particle diameter of 0.5 to 0.9 mm.

0.7 g of the prepared $ZnCr_{0.9}Al_{0.3}$ catalyst and 0.84 g of the prepared $AlPO_4$-5 were mixed and put into a quartz reaction tube with an inner diameter of 6 mm. Synthesis gas ($n_{H2}:n_{CO}$=50:50) was introduced into the reaction tube to enter the catalytic bed for reaction, with a reaction temperature of 400° C., a reaction system pressure of 4 MPa, and a gas hourly space velocity of 4,000 $h^{-1}$, so as to carry out the reaction of producing lower olefins with synthesis gas. The results of the activity evaluation were shown in Table 1.

Example 9

$ZnCr_{0.9}Al_{0.3}$ catalyst was prepared as in Example 8.
$AlPO_4$-11 catalyst was prepared by the following steps:
Pseudo-boehmite, phosphoric acid and diisopropylamine were respectively used as an aluminum source, a phosphorus source and a template agent, with molar ratios of $Al_2O_3$:$P_2O_5$:DIPA:$H_2O$=1:1:1:50, which were added into a reactor and then aged for 2 hours, and crystallized under stirring for 48 hours at 200° C. The obtained solid was washed to be neutral with deionized water, separated to obtain solid, dried, and roasted for 6 hours at 550° C. in a muffle furnace, to obtain the AlPO$_4$-11 molecular sieve.

All the formed catalysts had a 90% particle diameter of 0.5 to 0.9 mm.

0.7 g of the prepared ZnCr$_{0.9}$Al$_{0.3}$ catalyst and 0.84 g of the prepared AlPO$_4$-11 were mixed and put into a quartz reaction tube with an inner diameter of 6 mm. Synthesis gas (n$_{H2}$:n$_{CO}$=50:50) was introduced into the reaction tube to enter the catalytic bed for reaction, with a reaction temperature of 400° C., a reaction system pressure of 4 MPa, and a gas hourly space velocity of 4,000 h$^{-1}$, so as to carry out the reaction of producing lower olefins with synthesis gas. The results of the activity evaluation were shown in Table 1.

Example 10

ZnCr$_{0.9}$Al$_{0.3}$ catalyst was prepared as in Example 8.

AlPO$_4$-17 catalyst was prepared as in Example 2.

All the formed catalysts had a 90% particle diameter of 0.5 to 0.9 mm.

0.7 g of the prepared ZnCr$_{0.9}$Al$_{0.3}$ catalyst and 0.84 g of the prepared AlPO$_4$-17 were mixed and put into a quartz reaction tube with an inner diameter of 6 mm. Synthesis gas (n$_{H2}$:n$_{CO}$=50:50) was introduced into the reaction tube to enter the catalytic bed for reaction, with a reaction temperature of 400° C., a reaction system pressure of 4 MPa, and a gas hourly space velocity of 4,000 h$^{-1}$, so as to carry out the reaction of producing lower olefins with synthesis gas. The results of the activity evaluation were shown in Table 1.

Example 11

ZnCr$_{0.9}$Al$_{0.3}$ catalyst was prepared as in Example 8.

AlPO$_4$-18 catalyst was prepared as in Example 3.

All the formed catalysts had a 90% particle diameter of 0.5 to 0.9 mm.

0.7 g of the prepared ZnCr$_{0.9}$Al$_{0.3}$ catalyst and 0.84 g of the prepared AlPO$_4$-18 were mixed and put into a quartz reaction tube with an inner diameter of 6 mm. Synthesis gas (n$_{H2}$:n$_{CO}$=50:50) was introduced into the reaction tube to enter the catalytic bed for reaction, with a reaction temperature of 400° C., a reaction system pressure of 4 MPa, and a gas hourly space velocity of 4,000 h$^{-1}$, so as to carry out the reaction of producing lower olefins with synthesis gas. The results of the activity evaluation were shown in Table 1.

Example 12

ZnCr$_{0.9}$Al$_{0.3}$ catalyst was prepared as in Example 8.

AlPO$_4$-20 catalyst was prepared as in Example 4.

All the formed catalysts had a 90% particle diameter of 0.5 to 0.9 mm.

0.7 g of the prepared ZnCr$_{0.9}$Al$_{0.3}$ catalyst and 0.84 g of the prepared AlPO$_4$-20 were mixed and put into a quartz reaction tube with an inner diameter of 6 mm. Synthesis gas (n$_{H2}$:n$_{CO}$=50:50) was introduced into the reaction tube to enter the catalytic bed for reaction, with a reaction temperature of 400° C., a reaction system pressure of 4 MPa, and a gas hourly space velocity of 4,000 so as to carry out the reaction of producing lower olefins with synthesis gas. The results of the activity evaluation were shown in Table 1.

Example 13

ZnCr$_{0.9}$Al$_{0.3}$ catalyst was prepared as in Example 8.

AlPO$_4$-31 catalyst was prepared as in Example 5.

All the formed catalysts had a 90% particle diameter of 0.5 to 0.9 mm.

0.7 g of the prepared ZnCr$_{0.9}$Al$_{0.3}$ catalyst and 0.84 g of the prepared AlPO$_4$-31 were mixed and put into a quartz reaction tube with an inner diameter of 6 mm. Synthesis gas (n$_{H2}$:n$_{CO}$=50:50) was introduced into the reaction tube to enter the catalytic bed for reaction, with a reaction temperature of 400° C., a reaction system pressure of 4 MPa, and a gas hourly space velocity of 4,000 h$^{-1}$, so as to carry out the reaction of producing lower olefins with synthesis gas. The results of the activity evaluation were shown in Table 1.

Example 14

ZnCr$_{0.9}$Al$_{0.3}$ catalyst was prepared as in Example 8.

AlPO$_4$-34 catalyst was prepared as in Example 6.

All the formed catalysts had a 90% particle diameter of 0.5 to 0.9 mm.

0.7 g of the prepared ZnCr$_{0.9}$Al$_{0.3}$ catalyst and 0.84 g of the prepared AlPO$_4$-34 were mixed and put into a quartz reaction tube with an inner diameter of 6 mm. Synthesis gas (n$_{H2}$:n$_{CO}$=50:50) was introduced into the reaction tube to enter the catalytic bed for reaction, with a reaction temperature of 400° C., a reaction system pressure of 4 MPa, and a gas hourly space velocity of 4,000 h$^{-1}$, so as to carry out the reaction of producing lower olefins with synthesis gas. The results of the activity evaluation were shown in Table 1.

Example 15

ZnCr$_{0.9}$Al$_{0.3}$ catalyst was prepared as in Example 8.

AlPO$_4$-35 catalyst was prepared by the following steps:

Phosphoric acid, aluminum isopropoxide and hexamethylene imine were respectively used as a phosphorus source, an aluminum source and a template agent, with molar ratios of Al$_2$O$_3$:P$_2$O$_5$:HMI:H$_2$O=1:1.5:4.5:100, which were added into a reactor and then aged for 2 hours, and crystallized under stirring for 24 hours at 200° C. The obtained solid was washed to be neutral with deionized water, separated to obtain solid, dried, and roasted for 6 hours at 550° C. in a muffle furnace, to obtain the AlPO$_4$-35 molecular sieve.

All the formed catalysts had a 90% particle diameter of 0.5 to 0.9 mm.

0.7 g of the prepared ZnCr$_{0.9}$Al$_{0.3}$ catalyst and 0.84 g of the prepared AlPO$_4$-35 were mixed and put into a quartz reaction tube with an inner diameter of 6 mm. Synthesis gas (n$_{H2}$:n$_{CO}$=50:50) was introduced into the reaction tube to enter the catalytic bed for reaction, with a reaction temperature of 400° C., a reaction system pressure of 4 MPa, and a gas hourly space velocity of 4,000 so as to carry out the reaction of producing lower olefins with synthesis gas. The results of the activity evaluation were shown in Table 1.

Example 16

ZnCr$_{0.9}$Al$_{0.3}$ catalyst was prepared as in Example 8.

AlPO$_4$-44 catalyst was prepared by the following steps:

Pseudo-boehmite, phosphoric acid and triethylamine were respectively used as an aluminum source, a phosphorus source and a template agent, with molar ratios of Al$_2$O$_3$:P$_2$O$_5$:TEA:H$_2$O=1:1:1.5:60, which were added into a reactor and then aged for 2 hours, and crystallized under stirring for 24 hours at 180° C. The obtained solid was washed to be neutral with deionized water, separated to obtain solid, dried, and roasted for 6 hours at 550° C. in a muffle furnace, to obtain the AlPO$_4$-44 molecular sieve.

All the formed catalysts had a 90% particle diameter of 0.5 to 0.9 mm.

0.7 g of the prepared $ZnCr_{0.9}Al_{0.3}$ catalyst and 0.84 g of the prepared $AlPO_4$-44 were mixed and put into a quartz reaction tube with an inner diameter of 6 mm. Synthesis gas ($n_{H2}$:$n_{CO}$=50:50) was introduced into the reaction tube to enter the catalytic bed for reaction, with a reaction temperature of 400° C., a reaction system pressure of 4 MPa, and a gas hourly space velocity of 4,000 $h^{-1}$, so as to carry out the reaction of producing lower olefins with synthesis gas. The results of the activity evaluation were shown in Table 1.

Example 17

$ZnCr_{0.9}Al_{0.3}$ catalyst was prepared as in Example 8.
$AlPO_4$-56 catalyst was prepared by the following steps:
Phosphoric acid, aluminum isopropoxide and N,N,N',N'-tetramethyl-1,6-hexamethylene diamine were respectively used as a phosphorus source, an aluminum source and a template agent, with molar ratios of $Al_2O_3$:$P_2O_5$:TMHD:$H_2O$=1:1.1:2:50, which were added into a reactor and then aged for 2 hours, and crystallized under stirring for 24 hours at 200° C. The obtained solid was washed to be neutral with deionized water, separated to obtain solid, dried, and roasted for 6 hours at 550° C. in a muffle furnace, to obtain the $AlPO_4$-56 molecular sieve.

All the formed catalysts had a 90% particle diameter of 0.5 to 0.9 mm.

0.7 g of the prepared $ZnCr_{0.9}Al_{0.3}$ catalyst and 0.84 g of the prepared $AlPO_4$-56 were mixed and put into a quartz reaction tube with an inner diameter of 6 mm. Synthesis gas ($n_{H2}$:$n_{CO}$=50:50) was introduced into the reaction tube to enter the catalytic bed for reaction, with a reaction temperature of 400° C., a reaction system pressure of 4 MPa, and a gas hourly space velocity of 4,000 $h^{-1}$, so as to carry out the reaction of producing lower olefins with synthesis gas. The results of the activity evaluation were shown in Table 1.

Example 18

$ZnCr_{0.9}Al_{0.3}$ catalyst was prepared as in Example 8.
$AlPO_4$-34 catalyst was prepared as in Example 6.
All the formed catalysts had a 90% particle diameter of 5.0 to 5.5 mm.

0.7 g of the prepared $ZnCr_{0.9}Al_{0.3}$ catalyst and 0.84 g of the prepared $AlPO_4$-34 were mixed and put into a quartz reaction tube with an inner diameter of 6 mm. Synthesis gas ($n_{H2}$:$n_{CO}$=50:50) was introduced into the reaction tube to enter the catalytic bed for reaction, with a reaction temperature of 400° C., a reaction system pressure of 4 MPa, and a gas hourly space velocity of 4,000 $h^{-1}$, so as to carry out the reaction of producing lower olefins with synthesis gas. The results of the activity evaluation were shown in Table 1.

Example 19

$ZnCr_{0.9}Al_{0.3}$ catalyst was prepared as in Example 8.
$AlPO_4$-34 catalyst was prepared as in Example 6.
All the formed catalysts had a 90% particle diameter of 0.3 to 0.5 mm.

0.7 g of the prepared $ZnCr_{0.9}Al_{0.3}$ catalyst and 0.84 g of the prepared $AlPO_4$-34 were mixed and put into a quartz reaction tube with an inner diameter of 6 mm. Synthesis gas ($n_{H2}$:$n_{CO}$=50:50) was introduced into the reaction tube to enter the catalytic bed for reaction, with a reaction temperature of 400° C., a reaction system pressure of 4 MPa, and a gas hourly space velocity of 4,000 $h^{-1}$, so as to carry out the reaction of producing lower olefins with synthesis gas. The results of the activity evaluation were shown in Table 1.

Example 20

$ZnCr_{0.9}Al_{0.3}$ catalyst was prepared as in Example 8.
$AlPO_4$-34 catalyst was prepared as in Example 6.
All the formed catalysts had a 90% particle diameter of 0.5 to 0.9 mm.

0.7 g of the prepared $ZnCr_{0.9}Al_{0.3}$ catalyst and 0.84 g of the prepared $AlPO_4$-34 were mixed, which were immersed and loaded with 5% of Si using silica sol as a silicon source, and put into a quartz reaction tube with an inner diameter of 6 mm. Synthesis gas ($n_{H2}$:$n_{CO}$=50:50) was introduced into the reaction tube to enter the catalytic bed for reaction, with a reaction temperature of 400° C., a reaction system pressure of 4 MPa, and a gas hourly space velocity of 4,000 $h^{-1}$, so as to carry out the reaction of producing lower olefins with synthesis gas. The results of the activity evaluation were shown in Table 1.

Example 21

$ZnCr_{0.9}Al_{0.3}$ catalyst was prepared as in Example 8.
$AlPO_4$-34 catalyst was prepared as in Example 6.
All the formed catalysts had a 90% particle diameter of 0.5 to 0.9 mm.

0.7 g of the prepared $ZnCr_{0.9}Al_{0.3}$ catalyst and 0.84 g of the prepared $AlPO_4$-34 were mixed, which were immersed and loaded with 0.5% of vanadium using ammonium vanadate as a vanadium source, and put into a quartz reaction tube with an inner diameter of 6 mm. Synthesis gas ($n_{H2}$:$n_{CO}$=50:50) was introduced into the reaction tube to enter the catalytic bed for reaction, with a reaction temperature of 400° C., a reaction system pressure of 4 MPa, and a gas hourly space velocity of 4,000 $h^{-1}$, so as to carry out the reaction of producing lower olefins with synthesis gas. The results of the activity evaluation were shown in Table 1.

Example 22

$ZnCr_{0.9}Al_{0.3}$ catalyst was prepared as in Example 8.
$AlPO_4$-34 catalyst was prepared as in Example 6.
All the formed catalysts had a 90% particle diameter of 0.5 to 0.9 mm.

0.7 g of the prepared $ZnCr_{0.9}Al_{0.3}$ catalyst and 0.84 g of the prepared $AlPO_4$-34 were mixed, which were immersed and loaded with 0.3% of niobium using niobium oxalate as a niobium source, and put into a quartz reaction tube with an inner diameter of 6 mm. Synthesis gas ($n_{H2}$:$n_{CO}$=50:50) was introduced into the reaction tube to enter the catalytic bed for reaction, with a reaction temperature of 400° C., a reaction system pressure of 4 MPa, and a gas hourly space velocity of 4,000 $h^{-1}$, so as to carry out the reaction of producing lower olefins with synthesis gas. The results of the activity evaluation were shown in Table 1.

Example 23

$ZnCr_{0.9}Al_{0.3}$ catalyst was prepared as in Example 8.
$AlPO_4$-18 catalyst was prepared as in Example 3.
$AlPO_4$-34 catalyst was prepared as in Example 6.
All the formed catalysts had a 90% particle diameter of 0.5 to 0.9 mm.

0.7 g of the prepared $ZnCr_{0.9}Al_{0.3}$ catalyst, 0.084 g of the prepared $AlPO_4$-18 and 0.756 g of the prepared $AlPO_4$-34 were mixed and put into a quartz reaction tube with an inner diameter of 6 mm. Synthesis gas ($n_{H2}:n_{CO}$=50:50) was introduced into the reaction tube to enter the catalytic bed for reaction, with a reaction temperature of 400° C., a reaction system pressure of 4 MPa, and a gas hourly space velocity of 4,000 h$^{-1}$, so as to carry out the reaction of producing lower olefins with synthesis gas. The results of the activity evaluation were shown in Table 1.

Example 24

ZnCr$_{0.9}$Al$_{0.3}$ catalyst was prepared as in Example 8.
AlPO$_4$-18 catalyst was prepared as in Example 3.
AlPO$_4$-34 catalyst was prepared as in Example 6.
All the formed catalysts had a 90% particle diameter of 0.5 to 0.9 mm.
0.7 g of the prepared ZnCr$_{0.9}$Al$_{0.3}$ catalyst, 0.42 g of the prepared AlPO$_4$-18 and 0.42 g of the prepared AlPO$_4$-34 were mixed and put into a quartz reaction tube with an inner diameter of 6 mm. Synthesis gas ($n_{H2}:n_{CO}$=50:50) was introduced into the reaction tube to enter the catalytic bed for reaction, with a reaction temperature of 400° C., a reaction system pressure of 4 MPa, and a gas hourly space velocity of 4,000 h$^{-1}$, so as to carry out the reaction of producing lower olefins with synthesis gas. The results of the activity evaluation were shown in Table 1.

Example 25

ZnCr$_{0.9}$Al$_{0.3}$ catalyst was prepared as in Example 8.
AlPO$_4$-18 catalyst was prepared as in Example 3.
AlPO$_4$-34 catalyst was prepared as in Example 6.
All the formed catalysts had a 90% particle diameter of 0.5 to 0.9 mm.
0.7 g of the prepared ZnCr$_{0.9}$Al$_{0.3}$ catalyst, 0.756 g of the prepared AlPO$_4$-18 and 0.084 g of the prepared AlPO$_4$-34 were mixed and put into a quartz reaction tube with an inner diameter of 6 mm. Synthesis gas ($n_{H2}:n_{CO}$=50:50) was introduced into the reaction tube to enter the catalytic bed for reaction, with a reaction temperature of 400° C., a reaction system pressure of 4 MPa, and a gas hourly space velocity of 4,000 h$^{-1}$, so as to carry out the reaction of producing lower olefins with synthesis gas. The results of the activity evaluation were shown in Table 1.

Example 26

ZnCr$_{0.9}$Al$_{0.3}$ catalyst was prepared as in Example 8.
AlPO$_4$-18/AlPO$_4$-34 eutectic molecular sieve catalyst was prepared by the following steps:
Pseudo-boehmite, phosphoric acid, N,N,-diisopropylethylamine and triethylamine were respectively used as an aluminum source, a phosphorus source and a template agent, with molar ratios of Al$_2$O$_3$:P$_2$O$_5$:DIEA:TEA:H$_2$O=1:1:0.4:1.4:50, which were added into a reactor and then aged for 2 hours, and crystallized under stirring for 24 hours at 180° C. The obtained solid was washed to be neutral with deionized water, separated to obtain solid, dried, and roasted for 6 hours at 550° C. in a muffle furnace, to obtain the AlPO$_4$-18/AlPO$_4$-34 eutectic molecular sieve.
All the formed catalysts had a 90% particle diameter of 0.5 to 0.9 mm.
0.7 g of the prepared ZnCr$_{0.9}$Al$_{0.3}$ catalyst and 0.84 g of the prepared AlPO$_4$-18/AlPO$_4$-34 eutectic molecular sieve were mixed and put into a quartz reaction tube with an inner diameter of 6 mm. Synthesis gas ($n_{H2}:n_{CO}$=50:50) was introduced into the reaction tube to enter the catalytic bed for reaction, with a reaction temperature of 400° C., a reaction system pressure of 4 MPa, and a gas hourly space velocity of 4,000 h$^{-1}$, so as to carry out the reaction of producing lower olefins with synthesis gas. The results of the activity evaluation were shown in Table 1.

Example 27

ZnCrAl$_{0.2}$ catalyst was prepared by the following steps:
1 mol of zinc nitrate, 1 mol of chromic nitrate and 0.2 mol of aluminum nitrate were weighed, dissolved with 1000 mL of distilled water. Then, 6 mol of NaOH was dissolved in 1000 mL of water. The two aqueous solutions were combined and co-precipitated, then aged for 3 hours at 70° C., filtered, dried overnight at 100° C., and roasted for 12 hours at 400° C., to obtain the ZnCrAl$_{0.2}$ catalyst.
AlPO$_4$-35 catalyst was prepared as in Example 15.
All the formed catalysts had a 90% particle diameter of 0.5 to 0.9 mm.
1.2 g of the prepared ZnCrAl$_{0.2}$ catalyst and 0.3 g of the prepared AlPO$_4$-35 were mixed and put into a quartz reaction tube with an inner diameter of 6 mm. Synthesis gas ($n_{H2}:n_{CO}$=50:50) was introduced into the reaction tube to enter the catalytic bed for reaction, with a reaction temperature of 400° C., a reaction system pressure of 4 MPa, and a gas hourly space velocity of 4,000 h$^{-1}$, so as to carry out the reaction of producing lower olefins with synthesis gas. The results of the activity evaluation were shown in Table 1.

Example 28

ZnCrAl$_{0.2}$ catalyst was prepared as in Example 27.
AlPO$_4$-35 catalyst was prepared as in Example 15.
All the formed catalysts had a 90% particle diameter of 0.5 to 0.9 mm.
1.0 g of the prepared ZnCrAl$_{0.2}$ catalyst and 0.5 g of the prepared AlPO$_4$-35 were mixed and put into a quartz reaction tube with an inner diameter of 6 mm. Synthesis gas ($n_{H2}:n_{CO}$=50:50) was introduced into the reaction tube to enter the catalytic bed for reaction, with a reaction temperature of 400° C., a reaction system pressure of 4 MPa, and a gas hourly space velocity of 4,000 h$^{-1}$, so as to carry out the reaction of producing lower olefins with synthesis gas. The results of the activity evaluation were shown in Table 1.

Example 29

ZnCrAl$_{0.2}$ catalyst was prepared as in Example 27.
AlPO$_4$-35 catalyst was prepared as in Example 15.
All the formed catalysts had a 90% particle diameter of 0.5 to 0.9 mm.
0.5 g of the prepared ZnCrAl$_{0.2}$ catalyst and 1.0 g of the prepared AlPO$_4$-35 were mixed and put into a quartz reaction tube with an inner diameter of 6 mm. Synthesis gas ($n_{H2}:n_{CO}$=50:50) was introduced into the reaction tube to enter the catalytic bed for reaction, with a reaction temperature of 400° C., a reaction system pressure of 4 MPa, and a gas hourly space velocity of 4,000 h$^{-1}$, so as to carry out the reaction of producing lower olefins with synthesis gas. The results of the activity evaluation were shown in Table 1.

Example 30

ZnCrAl$_{0.2}$ catalyst was prepared as in Example 27.
AlPO$_4$-35 catalyst was prepared as in Example 15.
All the formed catalysts had a 90% particle diameter of 0.5 to 0.9 mm.

0.3 g of the prepared $ZnCrAl_{0.2}$ catalyst and 1.2 g of the prepared $AlPO_4$-35 were mixed and put into a quartz reaction tube with an inner diameter of 6 mm. Synthesis gas ($n_{H2}:n_{CO}$=50:50) was introduced into the reaction tube to enter the catalytic bed for reaction, with a reaction temperature of 400° C., a reaction system pressure of 4 MPa, and a gas hourly space velocity of 4,000 $h^{-1}$, so as to carry out the reaction of producing lower olefins with synthesis gas. The results of the activity evaluation were shown in Table 1.

Examples 31-36

The catalyst prepared in Example 14 was used in the reaction of synthesis gas to produce lower olefins, and the reaction conditions and evaluation results were shown in table 2.

Example 37

The catalyst prepared in Example 14 was loaded into a quartz reaction tube with an inner diameter of 6 mm, and synthesis gas ($n_{H2}:n_{CO}$=50:50) was introduced into the reaction tube to enter the catalytic bed for reaction, with a reaction temperature of 400° C., a reaction system pressure of 4 MPa, and a gas hourly space velocity of 4,000 $h^{-1}$, so as to carry out the reaction of producing lower olefins with synthesis gas. The results of the activity evaluation after 200 hours were shown in Table 4.

Comparative Example 1

$Zn_{3.5}CrAl$ and SAPO-34 were prepared according to the preparation process taught by [Science, 2016, 351, 1065-1068].
0.75 g of $Zn_{3.5}CrAl$ and 0.75 g of SAPO-34 were mixed and put into a quartz reaction tube with an inner diameter of 6 mm. Synthesis gas ($n_{H2}:n_{CO}$=50:50) was introduced into the reaction tube to enter the catalytic bed for reaction, with a reaction temperature of 400° C., a reaction system pressure of 4 MPa, and a gas hourly space velocity of 4,000 $h^{-1}$, so as to carry out the reaction of producing lower olefins with synthesis gas. The results of the activity evaluation were shown in Table 3.

Comparative Example 2

$ZnZr_2$ and SAPO-34 were prepared according to the preparation process taught by [Angewandte Chemie, 2016, 128, 4803-4806].
0.75 g of $ZnZr_2$ and 0.75 g of SAPO-34 were mixed and put into a quartz reaction tube with an inner diameter of 6 mm. Synthesis gas ($n_{H2}:n_{CO}$=50:50) was introduced into the reaction tube to enter the catalytic bed for reaction, with a reaction temperature of 400° C., a reaction system pressure of 4 MPa, and a gas hourly space velocity of 4,000 $h^{-1}$, so as to carry out the reaction of producing lower olefins with synthesis gas. The results of the activity evaluation were shown in Table 3.

Comparative Example 3

A supported iron-based catalyst was prepared according to the preparation process taught by patent document [CN102441383A].
1.50 g of $FeMnK/SiO_2$ catalyst was put into a quartz reaction tube with an inner diameter of 6 mm. Synthesis gas ($n_{H2}:n_{CO}$=50:50) was introduced into the reaction tube to enter the catalytic bed for reaction, with a reaction temperature of 400° C., a reaction system pressure of 4 MPa, and a gas hourly space velocity of 4,000 $h^{-1}$, so as to carry out the reaction of producing lower olefins with synthesis gas. The results of the activity evaluation were shown in Table 3.

Comparative Example 4

A FeZn—K catalyst was prepared according to the preparation process taught by patent document [CN102698764A].
1.50 g of FeZn—K catalyst was put into a quartz reaction tube with an inner diameter of 6 mm. Synthesis gas ($n_{H2}:n_{CO}$=50:50) was introduced into the reaction tube to enter the catalytic bed for reaction, with a reaction temperature of 400° C., a reaction system pressure of 4 MPa, and a gas hourly space velocity of 4,000 $h^{-1}$, so as to carry out the reaction of producing lower olefins with synthesis gas. The results of the activity evaluation were shown in Table 3.

Comparative Example 5

$ZnCr_{0.9}Al_{0.3}$ catalyst was prepared as in Example 8.
SAPO-34 catalyst was prepared by the following steps:
Phosphoric acid, pseudo-boehmite, ethyl orthosilicate and morpholine were respectively used as a phosphorus source, an aluminum source, a silicon source and a template agent, with molar ratios of $Al_2O_3:P_2O_5:SiO_2:MOR:H_2O$=1:1:0.6:3:100, which were added into a reactor and then aged for 2 hours, and crystallized under stirring for 24 hours at 200° C. The obtained solid was washed to be neutral with deionized water, separated to obtain solid, dried, and roasted for 6 hours at 550° C. in a muffle furnace, to obtain the SAPO-34 molecular sieve.
0.7 g of the prepared $ZnCr_{0.9}Al_{0.3}$ catalyst and 0.84 g of the prepared SAPO-34 were mixed and put into a quartz reaction tube with an inner diameter of 6 mm. Synthesis gas ($n_{H2}:n_{CO}$=50:50) was introduced into the reaction tube to enter the catalytic bed for reaction, with a reaction temperature of 400° C., a reaction system pressure of 4 MPa, and a gas hourly space velocity of 4,000 $h^{-1}$, so as to carry out the reaction of producing lower olefins with synthesis gas. The results of the activity evaluation were shown in Table 3.

Comparative Example 6

$ZnCr_{0.9}Al_{0.3}$ catalyst was prepared as in Example 8.
SAPO-34 catalyst was prepared as in Comparative Example 5.
SAPO-18 catalyst was prepared by the following steps:
N,N-diisopropylethylamine (DIEA) was used as a template agent, and orthophosphoric acid, pseudo-boehmite and ethyl orthosilicate were respectively used as a phosphorus source, an aluminum source, and a silicon source, with molar ratios of $Al_2O_3:P_2O_5:SiO_2:DIEA:H_2O$=1:0.9:0.4:1.8:100, which were crystallized under stirring for 24 hours at 200° C. The obtained solid was washed to be neutral with deionized water, separated to obtain solid, dried, and roasted for 6 hours at 550° C. in a muffle furnace, to obtain the SAPO-18 molecular sieve.
0.7 g of the prepared $ZnCr_{0.9}Al_{0.3}$ catalyst, 0.42 g of the prepared SAPO-34 and 0.42 g of the prepared SAPO-18 were mixed and put into a quartz reaction tube with an inner diameter of 6 mm. Synthesis gas ($n_{H2}:n_{CO}$=50:50) was introduced into the reaction tube to enter the catalytic bed for reaction, with a reaction temperature of 400° C., a reaction system pressure of 4 MPa, and a gas hourly space velocity of 4,000 $h^{-1}$, so as to carry out the reaction of producing lower olefins with synthesis gas. The results of the activity evaluation were shown in Table 3.

Comparative Example 7

$Zn_{3.5}CrAl$ and SAPO-34 were prepared according to the preparation process taught by [Science, 2016, 351, 1065-1068].

0.75 g of $Zn_{3.5}CrAl$ and 0.75 g of SAPO-34 were mixed and put into a quartz reaction tube with an inner diameter of 6 mm. Synthesis gas ($n_{H2}$:$n_{CO}$=50:50) was introduced into the reaction tube to enter the catalytic bed for reaction, with a reaction temperature of 400° C., a reaction system pressure of 4 MPa, and a gas hourly space velocity of 4,000 h$^{-1}$, so as to carry out the reaction of producing lower olefins with synthesis gas. The results of the activity evaluation for 200 hours were shown in Table 4.

TABLE 1

|  | CO adsorbing component | aluminophosphate molecular sieve | Ratio by weight | CO conversion/% | Ratio of olefins/paraffins |
|---|---|---|---|---|---|
| Example 1 | $Ga_2O_3$ + $Cr_2O_3$ | $AlPO_4$-5 | 1:1 | 40.8 | 10.50 |
| Example 2 | $Cr_2O_3$ | $AlPO_4$-17 | 1:1 | 42.6 | 14.01 |
| Example 3 | $ZnIn_{0.3}$ | $AlPO_4$-18 | 1:1 | 48.4 | 13.04 |
| Example 4 | $Ga_2O_3$ + $Zn_2Cr$ | $AlPO_4$-20 | 1:1 | 46.5 | 10.94 |
| Example 5 | $ZnCr_{0.8}In_{0.2}$ | $AlPO_4$-31 | 1:1 | 52.2 | 14.37 |
| Example 6 | $Zn_{0.7}Cr$ | $AlPO_4$-34 | 1:1 | 53.9 | 12.75 |
| Example 7 | $Zn_{0.2}/ZnCr_2$ | $AlPO_4$-5 | 1:1 | 47.5 | 10.82 |
| Example 8 | $ZnCr_{0.9}Al_{0.3}$ | $AlPO_4$-5 | 1:1.2 | 43.4 | 10.80 |
| Example 9 | $ZnCr_{0.9}Al_{0.3}$ | $AlPO_4$-11 | 1:1.2 | 43.4 | 10.72 |
| Example 10 | $ZnCr_{0.9}Al_{0.3}$ | $AlPO_4$-17 | 1:1.2 | 51.9 | 14.96 |
| Example 11 | $ZnCr_{0.9}Al_{0.3}$ | $AlPO_4$-18 | 1:1.2 | 53.9 | 19.94 |
| Example 12 | $ZnCr_{0.9}Al_{0.3}$ | $AlPO_4$-20 | 1:1.2 | 48.5 | 10.84 |
| Example 13 | $ZnCr_{0.9}Al_{0.3}$ | $AlPO_4$-31 | 1:1.2 | 50.0 | 12.94 |
| Example 14 | $ZnCr_{0.9}Al_{0.3}$ | $AlPO_4$-34 | 1:1.2 | 55.6 | 17.07 |
| Example 15 | $ZnCr_{0.9}Al_{0.3}$ | $AlPO_4$-35 | 1:1.2 | 52.9 | 14.43 |
| Example 16 | $ZnCr_{0.9}Al_{0.3}$ | $AlPO_4$-44 | 1:1.2 | 51.3 | 10.16 |
| Example 17 | $ZnCr_{0.9}Al_{0.3}$ | $AlPO_4$-56 | 1:1.2 | 48.7 | 10.78 |
| Example 18 | $ZnCr_{0.9}Al_{0.3}$ | $AlPO_4$-34 | 1:1.2 | 47.1 | 13.15 |
| Example 19 | $ZnCr_{0.9}Al_{0.3}$ | $AlPO_4$-34 | 1:1.2 | 52.1 | 14.91 |
| Example 20 | ($ZnCr_{0.9}Al_{0.3}$ + $AlPO_4$-34) + 5% Si | | 1:1.2 | 55.2 | 11.28 |
| Example 21 | ($ZnCr_{0.9}Al_{0.3}$ + $AlPO_4$-34) + 0.5% V | | 1:1.2 | 48.4 | 10.10 |
| Example 22 | ($ZnCr_{0.9}Al_{0.3}$ + $AlPO_4$-34) + 0.3% Nb | | 1:1.2 | 50.6 | 10.34 |
| Example 23 | $ZnCr_{0.9}Al_{0.3}$ | $AlPO_4$-18 10% $AlPO_4$-34 90% | 1:1.2 | 55.5 | 17.67 |
| Example 24 | $ZnCr_{0.9}Al_{0.3}$ | $AlPO_4$-18 50% $AlPO_4$-34 50% | 1:1.2 | 54.7 | 19.04 |
| Example 25 | $ZnCr_{0.9}Al_{0.3}$ | $AlPO_4$-18 90% $AlPO_4$-34 10% | 1:1.2 | 54.3 | 19.36 |
| Example 26 | $ZnCr_{0.9}Al_{0.3}$ | $AlPO_4$-18 30% $AlPO_4$-34 70% eutectic crystal | 1:1.2 | 55.2 | 19.54 |
| Example 27 | $ZnCrAl_{0.2}$ | $AlPO_4$-35 | 4:1 | 42.2 | 10.22 |
| Example 28 | $ZnCrAl_{0.2}$ | $AlPO_4$-35 | 2:1 | 45.1 | 11.30 |
| Example 29 | $ZnCrAl_{0.2}$ | $AlPO_4$-35 | 1:2 | 48.1 | 13.03 |
| Example 30 | $ZnCrAl_{0.2}$ | $AlPO_4$-35 | 1:4 | 43.9 | 11.37 |

TABLE 2

|  | Temperature/ ° C. | Pressure/ MPa | Space velocity/ h$^{-1}$ | CO conversion/ % | Ratio of olefins/ paraffins |
|---|---|---|---|---|---|
| Example 31 | 400 | 3 | 5000 | 51.1 | 29.89 |
| Example 32 | 380 | 8 | 4000 | 47.4 | 11.19 |
| Example 33 | 390 | 5 | 2000 | 52.6 | 13.76 |
| Example 34 | 410 | 2 | 8000 | 45.9 | 27.83 |
| Example 35 | 420 | 0.5 | 6000 | 49.2 | 18.13 |
| Example 36 | 430 | 1 | 7000 | 57.0 | 22.84 |

TABLE 3

|  | Catalyst | Ratio of olefins/paraffins |
|---|---|---|
| Example 14 | $ZnCr_{0.9}Al_{0.3}$ + $AlPO_4$-34 (weight ratio of 1:1.2) | 17.07 |
| Comparative Example 1 | $Zn_{3.5}CrAl$ + SAPO-34 (weight ratio of 1:1) | 4.54 |
| Comparative Example 2 | $ZnZr_2$ + SAPO-34 (weight ratio of 1:1) | 4.08 |
| Comparative Example 3 | FeMnK/$SiO_2$ | 3.23 |
| Comparative Example 4 | FeZn—K | 3.68 |
| Comparative Example 5 | $ZnCr_{0.9}Al_{0.3}$ + SAPO-34 (weight ratio of 1:1.2) | 4.82 |
| Comparative Example 6 | $ZnCr_{0.9}A_{0.3}$ + (50% SAPO-18 + 50% SAPO-34) (weight ratio of 1:1.2) | 5.37 |

TABLE 4

| Catalyst | | Ratio of olefins/ paraffins |
|---|---|---|
| Example 37 | ZnCr$_{0.9}$Al$_{0.3}$ + AlPO$_4$-34 (weight ratio of 1:1.2) | 14.92 |
| Comparative Example 7 | Zn$_{3.5}$CrAl + SAPO-34 (weight ratio of 1:1) | 2.38 |

The invention claimed is:

1. A molecular sieve composition comprising aluminophosphate molecular sieve particles and CO adsorbing particles, wherein:
 each CO adsorbing particle comprises at least one metal oxide selected from the group consisting of an oxide of Group IIB metal of the periodic table, an oxide of Group VIB metal of the periodic table, gallium oxide, and indium oxide,
 90% of the aluminophosphate molecular sieve particles have diameters ranging from 0.3 mm to 9 mm, and
 90% of the CO adsorbing particles have diameters ranging from 0.3 mm to 9 mm, and
 the molecular sieve composition does not comprise an SAPO molecular sieve.

2. The molecular sieve composition according to claim 1, wherein the aluminophosphate molecular sieve is at least one selected from the group consisting of AlPO$_4$-5, AlPO$_4$-11, AlPO$_4$-17, AlPO$_4$-18, AlPO$_4$-20, AlPO$_4$-31, AlPO$_4$-33, AlPO$_4$-34, AlPO$_4$-35, AlPO$_4$-44, and AlPO$_4$-56 and an intergrowth molecular sieve of AlPO$_4$-34 and AlPO$_4$-18.

3. The molecular sieve composition according to claim 1, wherein each aluminophosphate molecular sieve particle comprises AlPO$_4$-34 and AlPO$_4$-18 at a weight ratio of the AlPO$_4$-18 to the AlPO$_4$-34 of from 1:9 to 9:1.

4. The molecular sieve composition according to claim 1, wherein at least a part of the metal oxide exhibits a spinel structure according to XRD spectrum.

5. The molecular sieve composition according to claim 1, wherein a weight ratio of the aluminophosphate molecular sieve particles to the CO adsorbing particles is from 1:5 to 5:1.

6. The molecular sieve composition according to claim 1, wherein each CO adsorbing particle further comprises a binder.

7. The molecular sieve composition according to claim 6, wherein a weight ratio of the metal oxide to the binder is from 10:1 to 1:1.

8. The molecular sieve composition according to claim 1 is substantially free of at least one element selected from the group consisting of silicon, vanadium, and niobium.

9. The molecular sieve composition according to claim 1, wherein 90% of the aluminophosphate molecular sieve particles have diameters ranging from 0.4 mm to 5 mm, and/or 90% of the CO adsorbing particles have diameters ranging from 0.4 mm to 5 mm.

10. A process of preparing a molecular sieve composition of claim 1, comprising a step of combining the aluminophosphate molecular sieve particles and the CO adsorbing particles.

11. A process of producing lower olefins, comprising the step of contacting synthesis gas with the molecular sieve composition according to claim 1 to produce lower olefins.

12. The process according to claim 11 carried out at a reaction temperature of 320-480° C., a reaction pressure (gauge pressure) of 0.5-8 MPa, a gas hourly space velocity 800-10000 h$^{-1}$, and a volume ratio of CO to H$_2$ in the synthesis gas of 0.3-3.5.

13. The molecular sieve composition according to claim 1, wherein the aluminophosphate molecular sieve particles and the CO adsorbing particles are mechanically mixed with each other.

14. The molecular sieve composition according to claim 1, wherein each CO adsorbing particle comprises at least one metal oxide selected from the group consisting of zinc oxide, chromium oxide, gallium oxide, indium oxide, and a composite metal oxide of zinc oxide and chromium oxide.

15. The molecular sieve composition according to claim 2, wherein the aluminophosphate molecular sieve is at least one selected from the group consisting of AlPO$_4$-17, AlPO$_4$-18, AlPO$_4$-31, AlPO$_4$-33, AlPO$_4$-34, AlPO$_4$-35, and the intergrowth molecular sieve of AlPO$_4$-34 and AlPO$_4$-18.

16. The molecular sieve composition according to claim 3, wherein the weight ratio of the AlPO$_4$-18 to the AlPO$_4$-34 is from 1:3 to 3:1.

17. The molecular sieve composition according to claim 4, wherein at least 50% or more of the metal oxide exhibits the spinel structure according to XRD spectrum.

18. The molecular sieve composition according to claim 5, wherein the weight ratio of the aluminophosphate molecular sieve particles to the CO adsorbing particles ranges from 1:3 to 4:1.

19. The molecular sieve composition according to claim 6, wherein the binder is at least one selected from the group consisting of alumina, magnesia, titania, and zirconia.

20. The molecular sieve composition according to claim 7, wherein the weight ratio of the metal oxide to the binder ranges from 4:1 to 1.2:1.

21. The molecular sieve composition according to claim 9, wherein 90% of the CO adsorbing particles have diameters ranging from 0.5 mm to 0.9 mm.

* * * * *